(12) United States Patent
Piotrowski et al.

(10) Patent No.: US 10,022,274 B1
(45) Date of Patent: Jul. 17, 2018

(54) SYSTEMS AND METHODS FOR WOUND HEALING

(71) Applicants:Zdzislaw Harry Piotrowski, Oak Park, IL (US); Adam E. Piotrowski, Chicago, IL (US); Anna A. Piotrowski, Chicago, IL (US)

(72) Inventors: Zdzislaw Harry Piotrowski, Oak Park, IL (US); Adam E. Piotrowski, Chicago, IL (US); Anna A. Piotrowski, Chicago, IL (US)

( * ) Notice: Subject to any disclaimer, the term of this patent is extended or adjusted under 35 U.S.C. 154(b) by 316 days.

(21) Appl. No.: 14/728,769

(22) Filed: Jun. 2, 2015

Related U.S. Application Data

(60) Provisional application No. 62/006,755, filed on Jun. 2, 2014.

(51) Int. Cl.
*A61F 13/00* (2006.01)
*A61B 5/00* (2006.01)
*A61B 5/145* (2006.01)
*A61B 5/01* (2006.01)

(52) U.S. Cl.
CPC .......... *A61F 13/00068* (2013.01); *A61B 5/01* (2013.01); *A61B 5/145* (2013.01); *A61B 5/445* (2013.01); *A61F 13/00038* (2013.01); *A61F 2013/0017* (2013.01)

(58) Field of Classification Search
CPC .......... A61F 13/00051; A61F 13/00068; A61F 13/00038; A61F 5/026; A61F 5/028; A61B 5/01; A61B 5/145; A61B 5/445
USPC .................. 604/289; 128/888, 889, 846, 876
See application file for complete search history.

(56) References Cited

U.S. PATENT DOCUMENTS

| 2,367,690 | A | * | 1/1945 | Purdy | A61F 15/006 128/888 |
| 2,396,516 | A | * | 3/1946 | Lewis | A61F 5/00 5/604 |
| 3,722,508 | A | * | 3/1973 | Roberts | A61M 5/52 128/877 |
| 4,870,976 | A | * | 10/1989 | Denny | A61M 25/02 128/877 |

(Continued)

FOREIGN PATENT DOCUMENTS

| CN | 201578450 | 9/2010 |
| CN | 201710553 | 1/2011 |

OTHER PUBLICATIONS

Jarvie, Eleanor, and Jane E. Ramsay. "Obstetric management of obesity in pregnancy." Seminars in fetal and neonatal medicine. vol. 15. No. 2. WB Saunders, 2010, pp. 83-88.

(Continued)

*Primary Examiner* — Kim M Lewis
(74) *Attorney, Agent, or Firm* — Knobbe Martens Olson & Bear LLP

(57) ABSTRACT

Systems and methods can promote wound healing, including a wound dressing having a wound-facing surface and a second surface. The wound-facing surface can be configured to contact a wound of a patient. There can also be at least one conduit having an interior lumen operably connectable to the second surface of the wound dressing, a central window configured to allow air flow from the interior lumen of the conduit to the wound-facing surface of the wound dressing, and a flexible wrap operably connectable to the conduit.

20 Claims, 14 Drawing Sheets

(56) References Cited

U.S. PATENT DOCUMENTS

| | | | | |
|---|---|---|---|---|
| 5,018,534 | A | * | 5/1991 | Grant ................... A61M 25/02 128/877 |
| 6,270,469 | B1 | | 8/2001 | Mott |
| 6,629,942 | B1 | | 10/2003 | Tubbs |
| 7,934,507 | B2 | | 5/2011 | Brooks |
| 8,764,691 | B2 | | 7/2014 | Sharps et al. |
| 2005/0014451 | A1 | | 1/2005 | Wicks |
| 2005/0182344 | A1 | * | 8/2005 | Dixon ....................... A61F 5/30 602/1 |
| 2008/0200906 | A1 | * | 8/2008 | Sanders .............. A61M 1/0001 604/543 |
| 2009/0124988 | A1 | * | 5/2009 | Coulthard ........... A61M 1/0088 604/313 |
| 2009/0131892 | A1 | * | 5/2009 | Karpowicz ......... A61M 1/0088 604/313 |
| 2009/0293887 | A1 | * | 12/2009 | Wilkes ................... A61L 15/60 128/888 |

OTHER PUBLICATIONS

Johnson, A., D. Young, and Jv Reilly. "Caesarean section surgical site infection surveillance." Journal of Hospital Infection 64.1 (2006): 30-35.

Martens, M. G., et al. "Development of wound infection or separation after cesarean delivery. Prospective evaluation of 2,431 cases." The Journal of reproductive medicine 40.3 (1995): 171-175 (Abstract in 1 page).

Nicholson, S. C., et al. "'Classical' caesarean section at or near term in the morbidly obese obstetric patient." Journal of Obstetrics & Gynecology 22,6 (2002): 691.

Roberts, Scott, et al. "The microbiology of post-cesarean wound morbidity." Obsterics & Gynecology 81.3 (1993): 383-386.

Tipton, Amanda M., Stephen A. Cohen, and David Chelmow. "Wound infection in the obese pregnant woman." Seminars in perinatology. vol. 35, No. 6. WB Saunders, 2011.

* cited by examiner

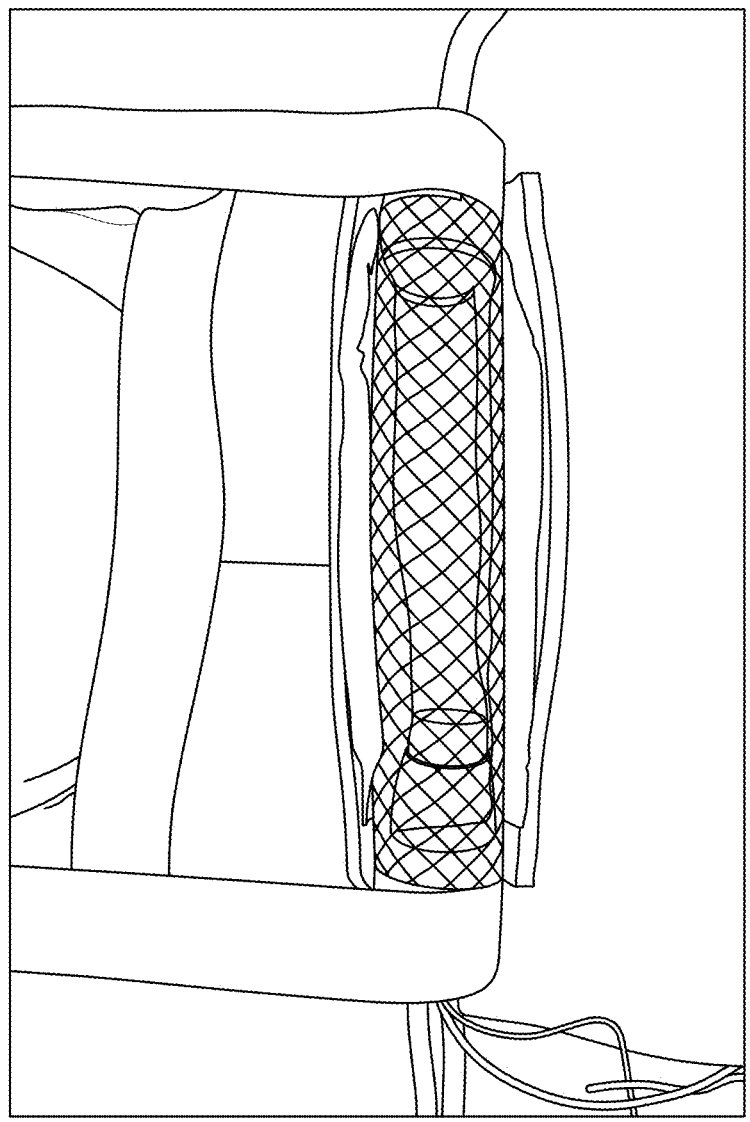

$$\left(p_s + \frac{\rho \bar{V}^2}{2}\right)_1 \quad \left(p_s + \frac{\rho \bar{V}^2}{2}\right)_2 \quad \text{Bernoulli Equation}$$

$$(P_p \times \int \frac{dA_p}{\ell}) \times \Delta p + (P_d \times \frac{A_d}{\ell_d}) \times \Delta p \quad \text{Moisture Diffusion Relationship (derivative from Fick's Law)}$$

(patient abdomen)

SYSTEMS AND METHODS FOR WOUND HEALING

CROSS-REFERENCE TO RELATED APPLICATIONS

This application claims the benefit under 35 U.S.C. § 119(e) as a nonprovisional application of U.S. Provisional Pat. App. No. 62/006,755 filed on Jun. 2, 2014 which is hereby incorporated by reference in its entirety.

BACKGROUND

Field of the Invention

The invention relates to, in some aspects, systems and methods for wound healing.

Description of the Related Art

Research has established that wound complications among overweight and obese women are higher compared to non-obese mothers. The American College of Obstetricians and Gynecologists (ACOG) released an official Committee Opinion in January 2013 stating, "Obese women who require cesarean delivery have an increased incidence of wound breakdown and infection." Conner et. al. presented a poster at the 2013 Society of Maternal Fetal Medicine that showed a 10.9% versus 6.6% incidence of wound complication for obese versus non-obese women.

Nationwide, there were approximately 727,000 cesarean deliveries by overweight and obese mothers in 2010. Considering an infection rate of 10% and a current cost between $3,382 to $10,443 per patient, the excess healthcare spending on this addressable problem is between $246M and $759M per year in the US. Additionally, because infection-related readmissions are now subject to reimbursement penalties hospitals are increasingly responsible for those costs.

Despite the latest technologies and improved techniques, surgical site infection ("SSI") following cesarean in overweight and obese women remains a challenge. While common procedures to reduce wound infections have certainly reduced the adverse outcomes, there is room for improvement. Current strategies which have been in place for several years may not go far enough. A new and novel addition is needed.

SUMMARY

Disclosed herein are systems for promoting wound healing. In some embodiments, the systems can include a wound dressing having a wound-facing surface and a second surface, the wound-facing surface configured to contact a wound of a patient; at least one conduit having an interior lumen, the conduit operably connectable to the second surface of the wound dressing, wherein the conduit comprises a central window configured to allow air flow from the interior lumen of the conduit to the wound-facing surface of the wound dressing; and a flexible wrap operably connectable to the conduit.

Also disclosed herein are methods for improving wound healing. Certain methods can include one or more of the following steps: identifying a patient at risk of wound dehiscence; positioning a wound care system comprising a wound dressing having a skin-contacting surface and a second surface, a conduit having an interior lumen connected to the second surface of the wound dressing, and a flexible wrap operably connected to the conduit proximate a wound of the patient's skin, and securing the wrap around a portion of the patient. The wound dressing can be positioned substantially co-linearly along a long axis of a wound of the patient's skin. Positioning the wound care system can stably reposition overhanging skin or adipose tissue surrounding the wound to a location farther away from the wound.

BRIEF DESCRIPTION OF THE DRAWINGS

FIG. 5B illustrate an embodiment of a wound care system including a conduit with a movable structure.

FIGS. 8A-8G illustrate perspective views of embodiments of wound care systems.

DETAILED DESCRIPTION

Figure 1:
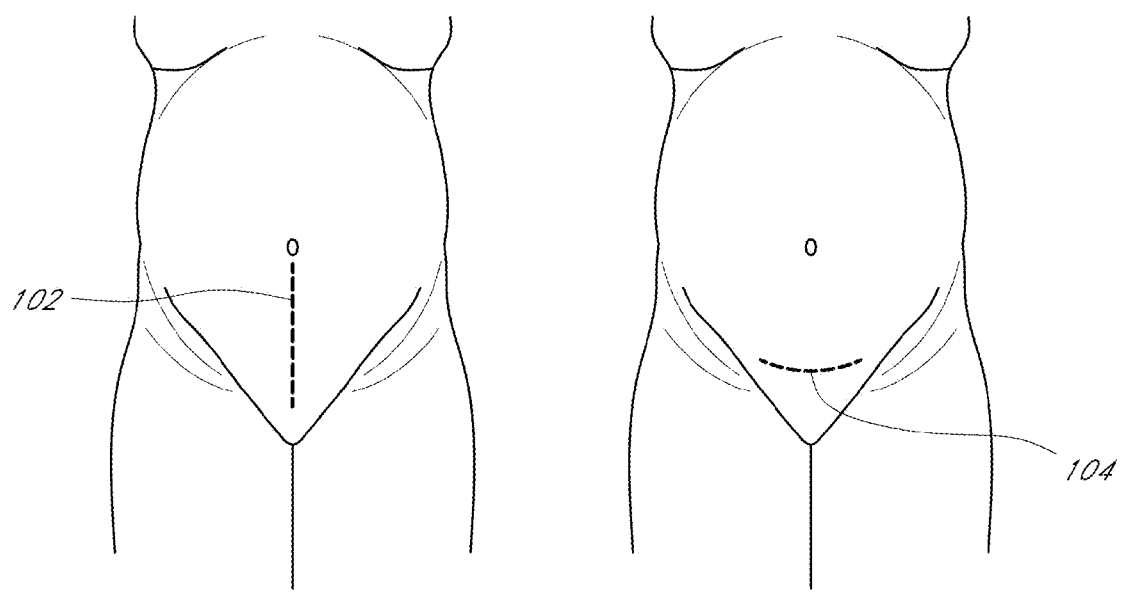
FIG. 1 illustrates two examples of abdominal surgical incisions.

In some embodiments, systems and methods disclosed herein can include a wound dressing material and an apparatus that provides an optimized wound healing environment for a wound or surgical incision. The extensive literature regarding the topic of wound healing and infection control of surgical incisions discusses the factors which contribute to and promote wound healing. A variety of intrinsic and extrinsic factors contribute to the timely, successful, and uncomplicated healing process. However, complications may often arise, as in the case of a patient with comorbidities, localized physiology, and localized morphology, and which may result in impaired wound healing and/or infection and/or abscess and/or any of the related complications regarding the aforementioned wound healing challenges.

In some embodiments, systems and methods can temporarily reposition body tissue surrounding and near a wound and encourage healing of a surgical or nonsurgical wound. In some embodiments, the systems are applied as a medical device and used by the patient for a period ranging from immediately post-surgery to a duration of weeks or beyond, a decision best determined by the practicing physician and team responsible for the patient's care. In some embodiments, systems and methods can provide one or more of the following: a wound dressing that provides structure to temporarily reposition skin/tissue during healing; adjustable tension and compression for optimal fit to the body; protects delicate incision site during healing; can control the micro environment around the peri-wound area to decrease wound healing complications; allows otherwise occluded wound site exposure to ambient environment to support and sustain natural wound healing; manages moisture and exudate from the skin and wound; provide cesarean incision wound healing monitoring and communicates status by combining pH, temperature, and relative humidity; and combine an abdominal compression binder with wound dressing pad without occluding the incision site.

Systems and methods as disclosed herein can, in some embodiments, counteract the often interruptive healing effects of excess and malpositioned tissue and adipose that can surround the wound and periwound regions. Excess tissue can complicate and inhibit the wound healing process when those tissues contact, fold, fold upon, overlay, occlude, abrade, irritate, and impact the incision area, wound bed, its surrounding area and tissue, and negatively affect the physiological and environmental variables associated with optimal wound healing and tissue vitality. Skin flora and other organisms can also potentially translocate into the wound, leading to wound infections. Devices as disclosed herein can temporarily reposition tissue proximate the wound such that it is no longer interfering and affecting the localized healing environment.

In some embodiments, systems and methods can incorporate active features, devices, and characteristics to enhance the healing environment in a positive aspect, such as controlling the air pressures and velocities to the wound surface.

The system and apparatus incorporate features and characteristics to enhance the localized healing environment, addressing variables and factors such as:
  ventilation
  temperature
  relative humidity
  surface moisture
  acoustics
  stresses, strains, e.g. shears, contact pressures, and normal forces (radial forces delivered via hoop stress of the apparatus)
  photoactivity
  microbial activity
  exudate management A non-limiting example of a wound in which this system may be used is to promote healing of a transverse incision in the abdominal area, such as one that a patient would receive if delivering a baby via cesarean section. Delivery by cesarean section may involve a variety of incisional approaches, developed over the years and discussed in the literature (e.g. Pfannenstiel, 'bikini', Joel-Cohen, etc). Typically, an incision is made in a transverse fashion in the lower abdominal area of the pregnant mother. The incision may be centered/mirrored symmetrically about the sagittal plane, asymmetrical to that plane, or a variation, all of which are discussed in the literature. FIG. 1 illustrates two examples of abdominal surgical incisions 101 on a patient's abdomen, including a vertical incision 102 on the left, and a horizontal incision 104 on the right, which can be a Pfannenstiel incision commonly used for Caesarean sections. Other non-obstetric related abdominal wounds can also be treated by systems and methods as described herein, including abdominal surgical wounds such as bowel resection, adhesionolysis, appendectomy, cholecystectomy, liver resection, Roux-en-Y, and other procedures involving an abdominal incision, as well as gunshot, stab and other traumatic wounds, and fistulas. Non-abdominal wounds such as chest or other sternotomy incisions, scalp/cranial, upper extremity, lower extremity, spinal/back or hip incisions/wounds, or diabetic leg or foot ulcers for example can also be treated using systems and methods as described herein.

In the case of a pregnant mother of normal, elevated, high, or extremely high (and beyond) body mass index (BMI), who delivers via a cesarean section, there may be complications of wound healing related to the physical manifestations of tissue in the area of the wound bed and the surrounding area of the incision site. The surrounding tissue may be positioned over, adjacent, or against the incision site, resulting in a variety of negative factors such as (any, all, or a combination thereof):
  occlude the wound and surrounding tissue from exposure to the environment;
  not allowing the wound and its dressing to 'breathe';
  create a state of elevated temperature and moisture;
  result in maceration of surrounding tissues and the wound;
  encourage growth and proliferation of bacteria and microbes;
  decrease photoactivity (exposure to light) from the environment;
  reduce or impair ventilation across and over the wound bed and surrounding tissues; and
  affect the skin forces around the wound bed and surround tissue.

In some embodiments, systems and methods can include identifying patients at risk for poor wound healing, including patients with a BMI of at least about 25, 26, 27, 28, 29, 30, 31, 32, 33, 34, 35, 36, 37, 38, 39, 40, 41, 42, 43, 44, 45, or more, and applying a system such as those disclosed herein. In some embodiments, patients at risk for poor wound healing can be identified by the presence of one or more risk factors for poor wound healing, including but not limited to advanced age, smokers, diabetes, malnourished patients, alcoholism, corticosteroid use, chronic kidney disease, peripheral vascular disease, previous history of poor wound healing, and the like.

In some embodiments, systems and methods as disclosed herein can counteract the often interruptive healing effects of excess and malpositioned tissue and adipose that surround the wound and periwound regions. Excess tissue can complicate and inhibit the wound healing process when those tissues contact, fold, fold upon, overlay, occlude, abrade, irritate, and impact the incision area, wound bed, its surrounding area and tissue, and negatively affect the physiological and environmental variables associated with optimal wound healing and tissue vitality. In some embodiments, the system can temporarily reposition the tissue such that it is no longer interfering and affecting the localized healing environment.

Figure 2:
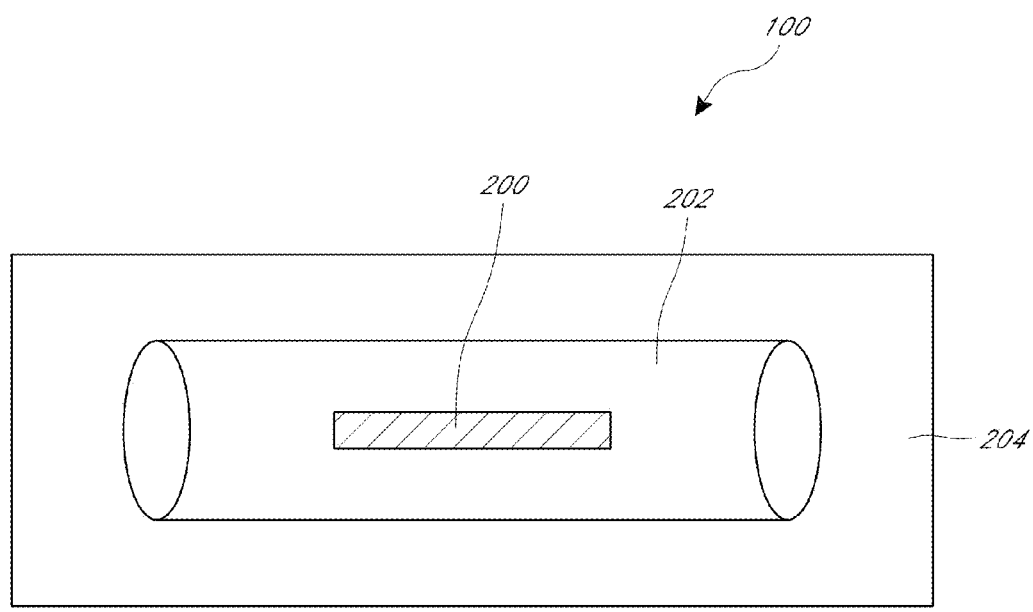
FIG. 2 illustrates an embodiment of a wound care system 100, including a wound dressing, a conduit, and a wrap.

In some embodiments, wound healing systems can incorporate features, devices, and characteristics to enhance the healing environment in a positive aspect, such as controlling the air pressures and velocities to the wound surface. For example, in some embodiments, features and characteristics of systems to enhance the localized healing environment can address variables and factors such as:

ventilation
temperature
relative humidity
surface moisture
acoustics
stresses, strains, e.g. shears, contact pressures, and normal forces (radial forces delivered via hoop stress of the apparatus)
photoactivity
microbial activity
exudate management FIG. 2 illustrates an embodiment of a wound care system 100. Wound care system 100 can include a wound dressing 200, one, two, or more conduits 202, and a wrap 204. The wound dressing 200 can include a wound-facing surface and a surface opposite the wound-facing surface. The wound-facing surface of the wound dressing 200 can be configured to rest against a patient's skin, such as proximate or within the wound. The surface opposite the wound-facing surface can be operably attached to the conduit 202. The conduit 202 can operably be attached to a wrap 204, such as an abdominal binder, ACE wrap, or the like.

The wound dressing 200 can be comprised of a number of dressings, such as gauze including cotton and Vaseline gauze, hydrocolloids, alginates, hydrophilic polyurethane foams, silver antimicrobials, copper or other ionic antimicrobials, gauze with additional antimicrobial additives, growth factors (including EGF, KGF, IGF, PDFT, TGF, FGF, VEGF, and others), and foam with and without additives.

Figure 3A:
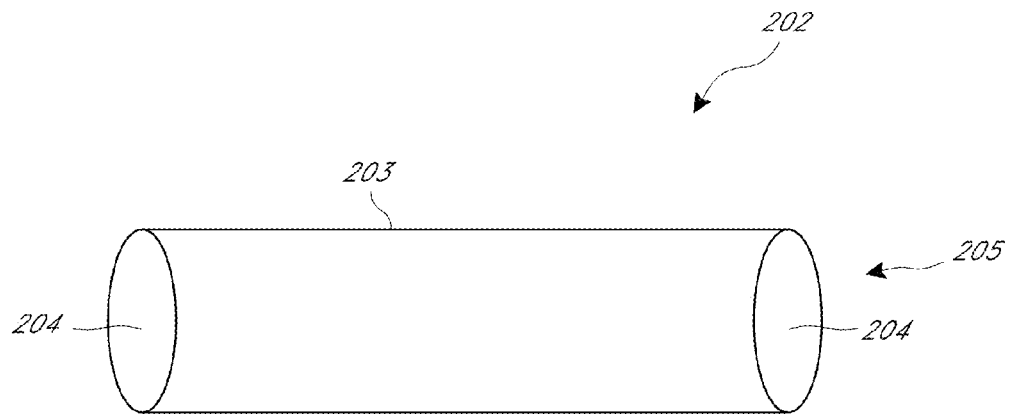
FIG. 3A illustrates an embodiment of a conduit having a sidewall, interior lumens, and closed or open ends.
Figure 3B:
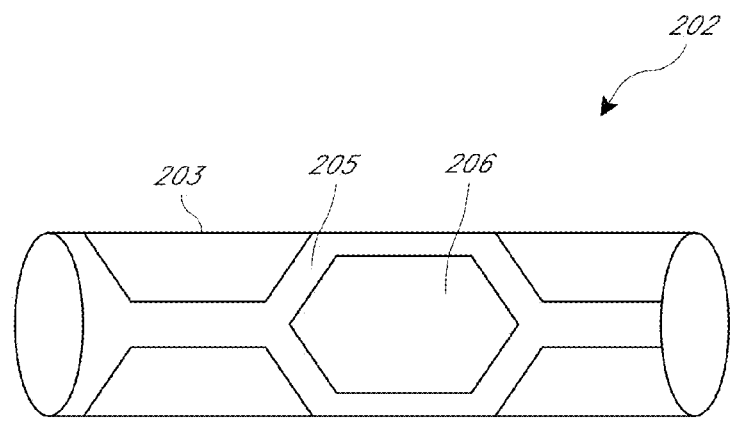
FIG. 3B illustrates an embodiment of a conduit with a sidewall having open areas and trussed regions such as struts.

The conduit 202 can be configured to temporarily reposition overhanging tissue around the wound bed, creating a direct or indirect conduit to the ambient or external environment. In some embodiments, the conduit 202 can have a generally tubular (e.g., cylindrical) structure with a circular, oval, or other symmetric or asymmetric cross-section. As illustrated in FIG. 3A, the conduit 202 can have a sidewall 203, one, two, or more interior lumens 205, and closed or open ends 204 (or one closed and one open end). In some embodiments, the sidewall 203 can be continuous, or non-continuous (such as forming a "C" shaped cross-section for example) and either permeable or non-permeable. In some embodiments, the sidewall 203 of the conduit 202 can have open areas 206 and trussed regions 205 such as struts as illustrated in FIG. 3B. The function of the continuous sidewall 203, or trussed regions 205, in some embodiments, is to counteract forces imparted by the tissue which is temporarily repositioned, and to maintain a lumen or conduit to the environment that can remain patent during typical motion and activities of the user.

In some embodiments, the axial length of the conduit 202 can range from approximately 3 inches to approximately 40 inches. The conduit 202 can be substantially the same length as, or longer than the axial length of the wound dressing 200, such as at least about 10%, 20%, 30%, 40%, 50%, 75%, 100%, 150%, 200%, 250%, 300%, or more longer than the axial length of the wound dressing 200. The diameter of the conduit 202 can vary in some embodiments from about 0.25 inches to about 4 inches in order to accommodate patients of a variety of shapes and sizes. The radius may optionally be non-constant and the cross section may be asymmetric or symmetric.

The wound care device can be secured in direct contact to the skin surface on the wearer with, for example, adhesive or in combination with a wrap, such as an abdominal binder. The binder can include an adjustable strap and fastener that allows easy application or removal of the device.

Figure 3C:
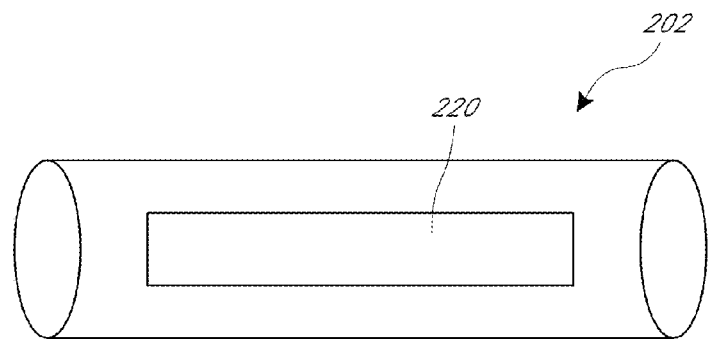
FIG. 3C illustrates an embodiment of a conduit with a central window.

In some embodiments, as illustrated in FIG. 3C, one or more window portions 220 such as a cut-out can be present between the two ends 204 of the conduit 202, such as near the center of the conduit 202. This is where the wound dressing (not shown for clarity) overlays the wound bed and is in contact with the healing wound. The cutaway window 220 can, in some embodiments, have dimensions of about 3 inches to about 12 inches in length and a height approximately 1 to 4 inches. The corners and edges of the cutout window may optionally be round, smooth, or radiused as to improve the interface between the wound care device and the skin. Additionally, in some embodiments, the inner edge of the window 220 can include a co-molded or added-on lip or gasket of a soft material, such as silicone, which provides a gradient transition between the less flexible, more rigid conduit 202 and the cutaway where the wound dressing overlays the wound bed and surrounding area. The conduit matrix can also overlay on surrounding tissue areas surrounding the wound bed.

Figure 3D:
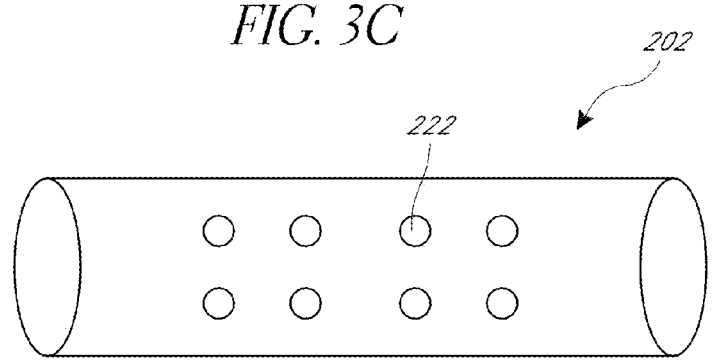
FIG. 3D illustrates an embodiment of a conduit with a plurality of central apertures.
Figure 3E:
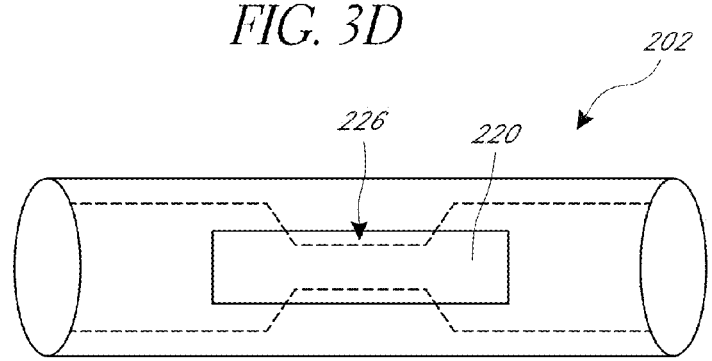
FIG. 3E illustrates an embodiment of a conduit that includes a restriction within the interior lumen.

In some embodiments, instead of a window 220, as illustrated in FIG. 3D, a conduit 202 can include a series of apertures 222 to provide a path for communication to the wound dressing. The number, size, and spacing of the apertures can vary depending on the desired clinical result. The apertures can be generally centrally located along the conduit 202 in some embodiments. In some embodiments, rather than discrete apertures the zone that would contain the window 220 or the apertures 222 could be made of a porous material to provide the communication to the wound dressing.

The conduit 202 can include a hollow core or lumen, which contacts the non-wound-contacting side of the wound dressing, and is bound by the interior surface, e.g., inner diameter of the conduit 202. The exterior surfaces of the conduit 202 can be configured to interface, displace, and/or temporarily move the tissue and adipose surrounding the wound. The interior lumen of the conduit 202 can be left open/hollow, partially filled with additional wound management materials like foams, dressings, and moisture absorbing materials, or completely filled for example by a matching foam core, which may be attached to a mechanized system to manage wound exudate.

The exterior surfaces, e.g., outer diameter of the conduit 202 may optionally include a laminate layer(s) of moisture-absorbing material such as alginate, hydrogels, foams and other hydrophilic materials and compositions. The function of the moisture management is to absorb excess sweat and other body fluids and ambient environment which if present may create a sub-optimal wound healing environment.

The interior shape of the lumen of the conduit 202 can be designed such that airflow and velocity of passing air currents is optimized to create a Venturi effect. The Venturi effect can lower the local pressure by increasing the velocity of the fluid passing through a constriction. In this example the fluid is ambient or filtered air. Similarly, the interior lumen of the conduit 202 can enhance airflow across the distal surface of the dressing. As such, the conduit can include a constriction region 226 with a decreased inner diameter akin to the midportion of an hourglass. The constriction region 226 can be proximate or coextensive with the window/aperture/porous zone of the conduit 202 communicating with the wound dressing 200.

In some embodiments, the wound care system can include active components rather than being entirely passive. An active conduit 202 could incorporate one or a plurality of a mechanical valve and sensor assembly in order to modulate the conditions within the interior surfaces and lumen of the apparatus, accelerative or decelerating moving air currents based on the undulations and presence/absence of a pump or fan element to augment the velocity of air currents.

The flow of air currents within the conduit can provide a cooling effect, which counteracts the moisture on the skin surfaces and within the skin and the temperature increases which result from tissue to tissue contact in patients with excess tissue and adipose. The ideal temperature for wound healing is, in some embodiments that of the human body's optimal temperature range, such as about 37° C. An optional configuration of the conduit includes the inclusion of sensors which can record and communicate the temperature, relative humidity, and/or other parameters in the wound bed area and surrounding tissue areas. The sensors can be positioned, for example, in the center, ends, and/or peripheries of the wound area.

Figure 3F:
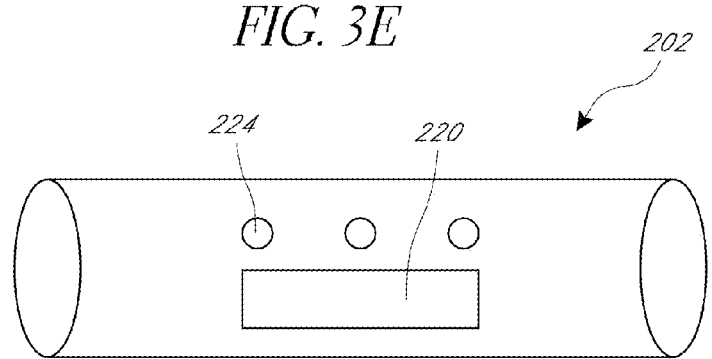
FIG. 3F illustrates an embodiment of a conduit that includes sensors operably attached to the conduit and adjacent the wound dressing.

In some embodiments, as shown in FIG. 3F, the sensors 224 can be operably attached to the conduit 202 and adjacent to the wound dressing 200 to communicate parameters such as temperature, humidity, and/or pH (e.g., the acidity/alkalinity of the wound bed environment and surrounding tissue area). The sensor information may be interpreted in order to understand the local pH of the wound bed and surrounding tissue area, which may change in the event of a wound infection, for example, empowering the patient and physician to perform earlier stage interventions (such as starting or changing antibiotic therapy, or performing a debridement procedure) at potentially a lower cost.

The wound dressing and the conduit can work harmoniously as a temporary support and tissue displacement structure and surgical wound dressing to optimize the acute environment surrounding the healing and care of a wound or surgical incision. The wound dressing maintains access to the ambient environment via support structures (e.g., the conduit) and reduces exposure to the factors which precede infection and poor recovery outcomes.

Figures 4A, 4B:
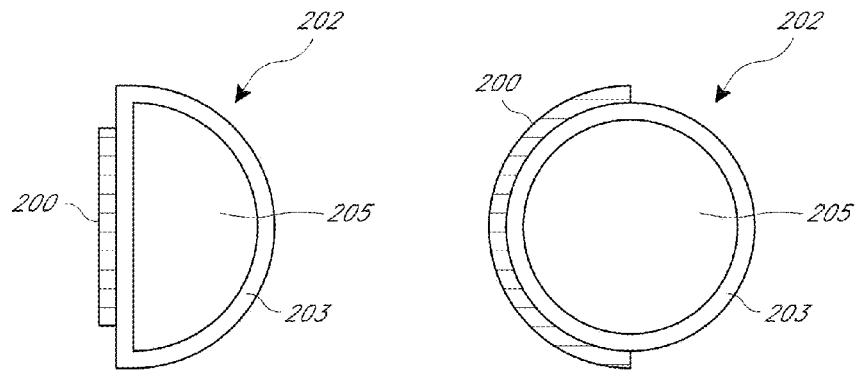
FIGS. 4A-4C illustrate various embodiments of cross sections of portions of wound care systems.
Figure 4C:
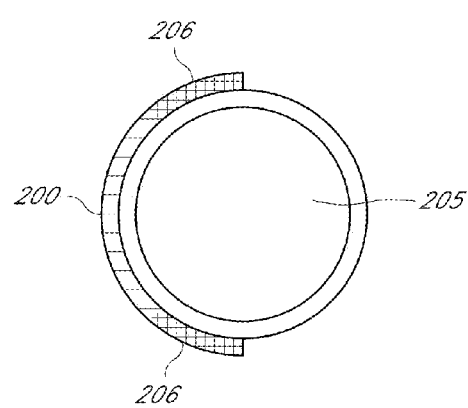

FIGS. 4A-4C illustrate various embodiments of cross sections of portions of wound care systems. The conduit 202 may compress and deform, but it can be designed such that it does not fully collapse upon itself. A tube is one possible embodiment, because the arc and curved surfaces distribute loads and reduce tendency for the tube to crush. The cross-sectional profile of the conduit 202 may optionally be a hexagon, septogon, octogon, or any other n-gon, up to circular, where n approximates infinity, as illustrated schematically in FIG. 4B, illustrating the conduit sidewall 203 and cross-section of the lumen 205, and also showing wound care dressing 200 operably connected to conduit 202. Alternatively, the luminal cross-section 205 of the conduit can be asymmetric, as illustrated in FIG. 4A. As illustrated in FIG. 4C, conduit 202 can also include an adhesive layer 206 for temporarily adhering to the surface of skin surrounding the conduit 202.

Figure 5A:
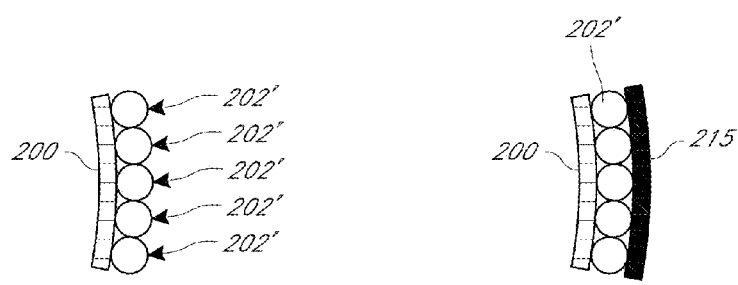
FIG. 5A illustrate an embodiment of a wound care system including a conduit with a plurality of lumens.

In some embodiments, as illustrated in FIG. 5A the conduit 202 may be made up of a plurality of lumens 202', such as 2, 3, 4, 5, or more lumens. Each lumen can be in communication with the wound dressing 200, to allow moisture and air to pass from the wound bed to the bandage 200 and through the lumens 202'.

In some embodiments, the conduit 202 includes one or more movable parts or structures, such as living joints/hinges, snap joints, fabricated flexures, heat-shrinked joints or flexures, welded joints, simple mechanical hinges, pinned hinges, flexible hinges, or the like. The type of movable structure depends on the type of manufacturing. Examples of different types of manufacturing of the conduit and movable structures can be blow molding, heat sealing, overmolding, the mechanical assembly of a rigid paneled chassis with a flexible bladder or skin to form the body, coining to form living hinges, assembly using gaskets as seals in hinges, injection molding, ultrasonic welding, radio frequency welding, dielectric welding, high frequency welding, dipping, extrusion, spray coating, brush on, assembly of adhesive backed sheets of various materials, and/or any type of manufacturing that results in a body with panels that are movable with respect to each other. Movable structures, e.g., hinge 215, is shown in the cross-section of FIG. 5B. The hinge 215 can be located distally opposite the incision and may be integrated into the conduit 202 in any number of ways, such as a co-molded and as a manufactured living hinge 215. The hinge 215 can provide a compressive force, in situations where the conduit has a bias to decrease its diameter and close. In this optional embodiment, the resulting effect is to unload the periwound area, thereby reducing tension across the wound bed and the incision, which could potentially improve outcomes. The conduit 202 can act as a longitudinal clip or clamp which reduces the separation forces across a wound or incision and promotes healing. The window, apertures, or porous material as described above can be utilized with this embodiment as well.

In some embodiments, the wound care system can be a combination of dressing and conduit to make one device, where the wound dressing is interchangeable, or optionally, it may be supplied as a single-use device and the wound dressing and supporting apparatus are interconnected and not interchangeable.

The conduit can also include other features, including but not limited to bilateral laterally-extending lumens 309 or "snorkels," as illustrated in FIGS. 8B-8G below, which may have a smaller, the same, or a larger inner or outer diameter than a lumen of the conduit 202. One function of these snorkels 309 is to interface the conduit 202 to the exterior environment. The snorkel 309, the conduit 202, and the abdominal binder 204 can be conformable such that when applied to a patient they interface with the patient and tissue of the wound bed and surrounding wound area. The snorkels 309 can exit through a slit or reinforced port in the abdominal binder 204.

If the patient would like to shower with their device, something that many wound dressings prohibit, removable end caps can be placed over the lumens and port holes of the conduit. These end caps interface with the cross sectional profiles and areas at the longitudinal ends of the apparatus and when implemented temporarily, contribute a water resistance which allows the patient to shower or rinse without compromising the wound nor the wound dressing. In some embodiments, rather than end caps, the ends of the conduit can include a valve with a control in which the patient can open and close the valve at appropriate times, such as before or after washing.

Figure 6:
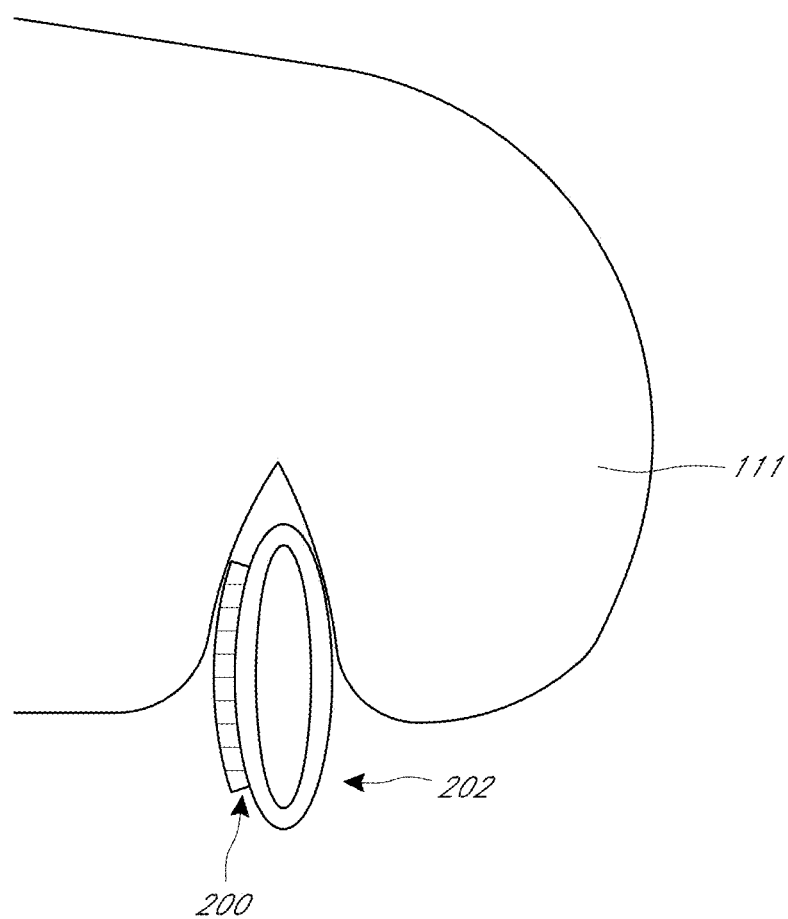
FIG. 6 schematically illustrates a wound care system repositioning overhanging tissue proximate a wound.

In some embodiments, the device can be worn and applied collinearly along the wound or incision line, and positioned underneath overhanging skin or tissue adipose. As shown schematically in FIG. 6, the wound care system, including the conduit 202 can temporarily and advantageously reposition overhanging tissue 111 around the wound bed 101 such that the adjacent overhanging tissue does not contact the wound bed 101 nor the wound dressing 100, and also advantageously creating a direct or indirect conduit to the ambient or external environment.

Figure 7A:
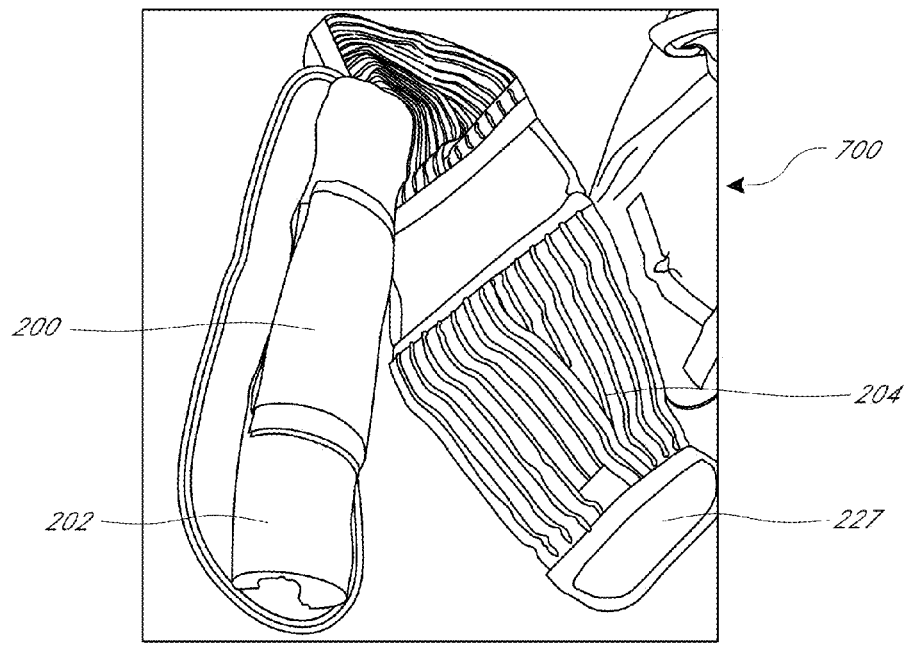
FIGS. 7A and 7B illustrate perspective views of a wound care system including wound care dressing, conduit, and wrap.
Figure 7B:
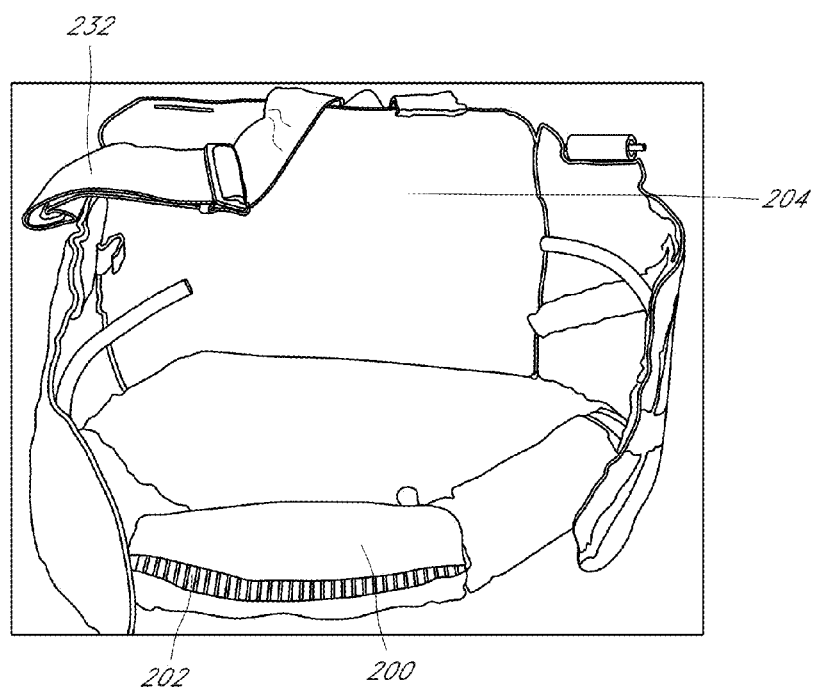

FIGS. 7A and 7B illustrate perspective views of a wound care system 700 including wound care dressing 200, conduit 202, and wrap 204 as described elsewhere herein. The wrap 204 can include an abdominal binder with fasteners 227 such as clips or hook-and-loop fastener material, for example. Also illustrated in FIG. 7B are straps 232 which can be placed over the patient's shoulders, for example for additional support.

Figure 8A:
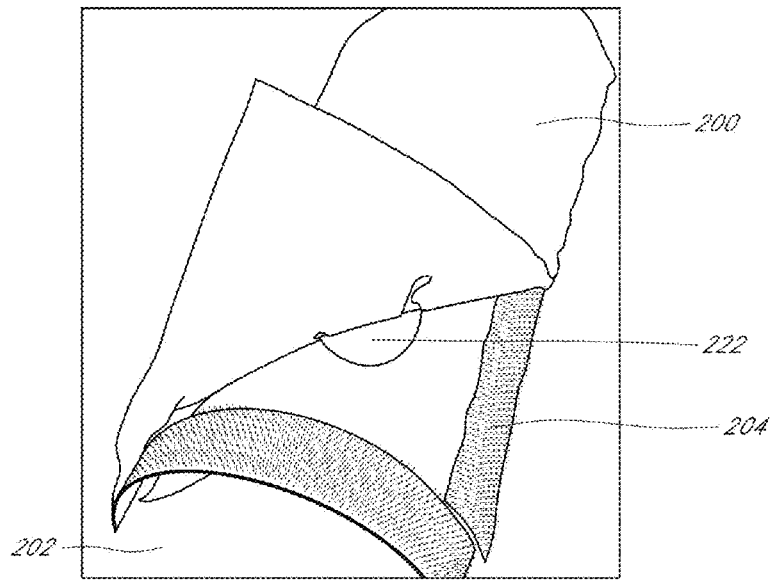
Figure 8B:
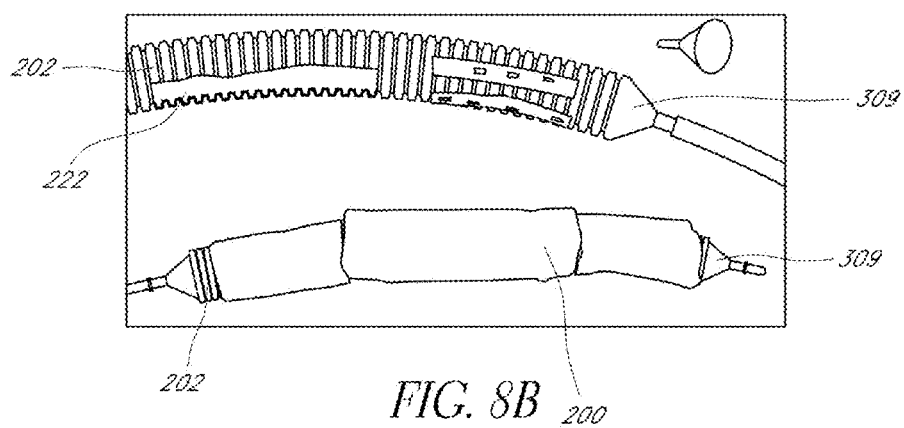

FIG. 8A illustrates a perspective view of a conduit 202 with a window 222 portion as previously described. Outer surface of the conduit 202 can include a connector 204, such as a perimeter of hook-and-loop fastener material to which a wound dressing 200 can removably attach to. Adhesive, clips, snap-on fasteners, and other attachment mechanisms can also be utilized. The upper portion of FIG. 8B illustrates a tubular conduit 202 with window 220 and lateral snorkel portion 309 as previously described. The lower portion of FIG. 8B illustrates a tubular conduit 202 with wound dressing 200 attached along a portion of the outer circumference of the conduit 202.

Figure 8C:
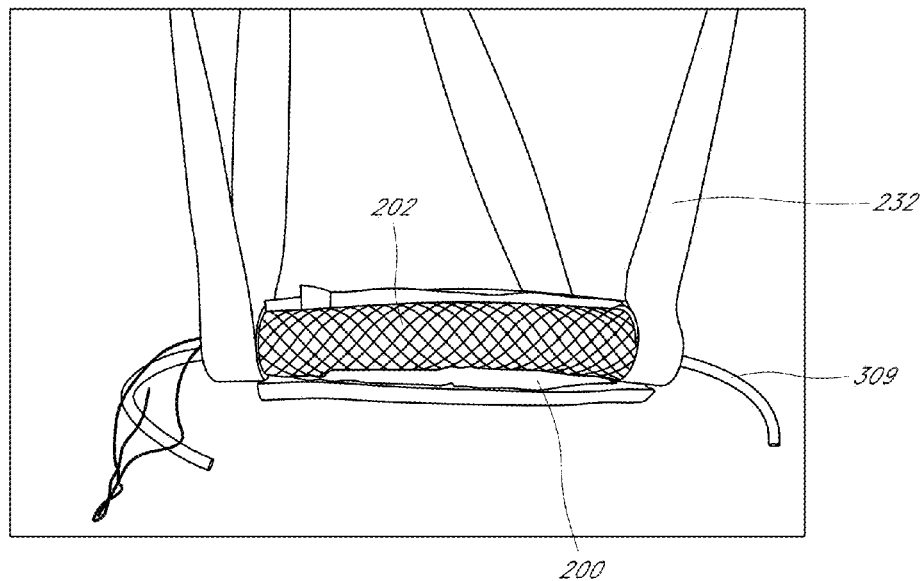
Figure 8D:
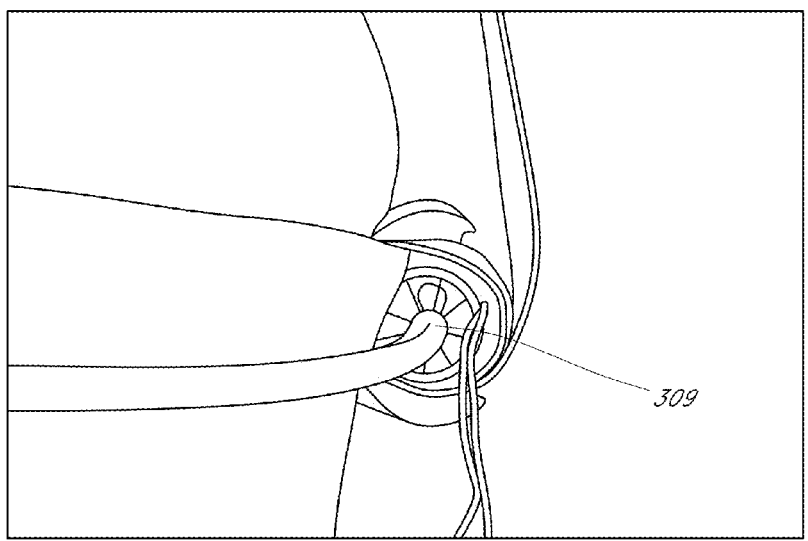
Figure 8E:
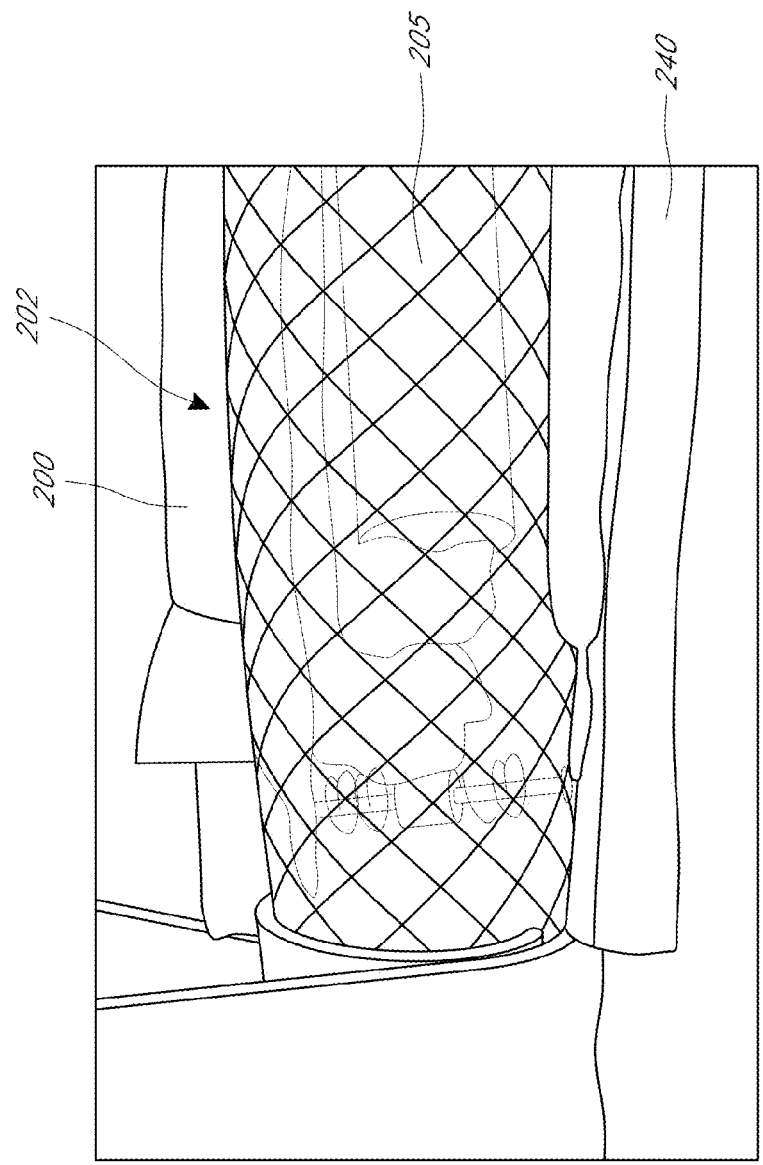
Figure 8G:
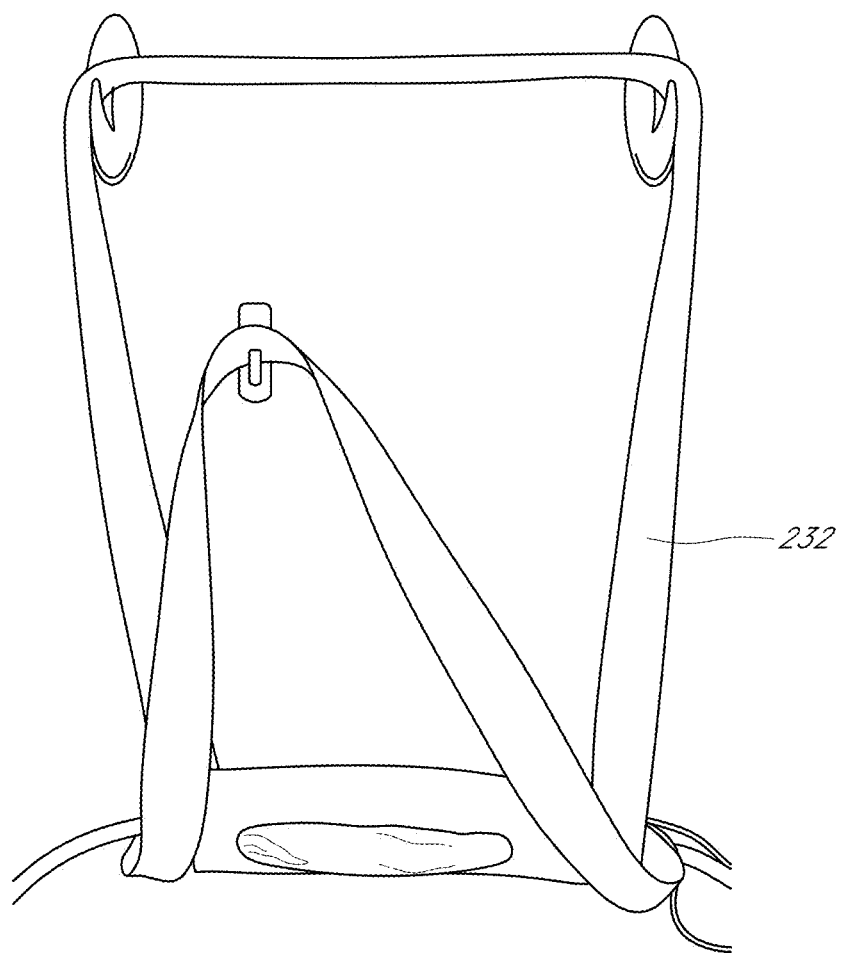

FIG. 8C illustrates a perspective view of a wound care system including conduit 202 formed with intersecting struts, lateral snorkels 309 wound dressing 200, and straps 232. FIG. 8D illustrates an end perspective view of a device with snorkel 309. FIG. 8E illustrates a close-up view illustrating the tubular conduit 202 with struts 205, and additional peri-wound material layer 240 surrounding the conduit 202 and the wound dressing 200. FIG. 8F illustrates another perspective view of the device. FIG. 8G illustrates a perspective view of device including straps 232.

Figure 9:
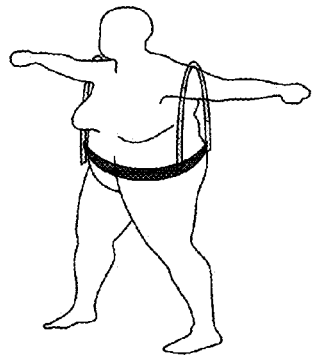
FIG. 9 illustrates schematically the positioning of the device transversely across the abdomen.
Figure 10:
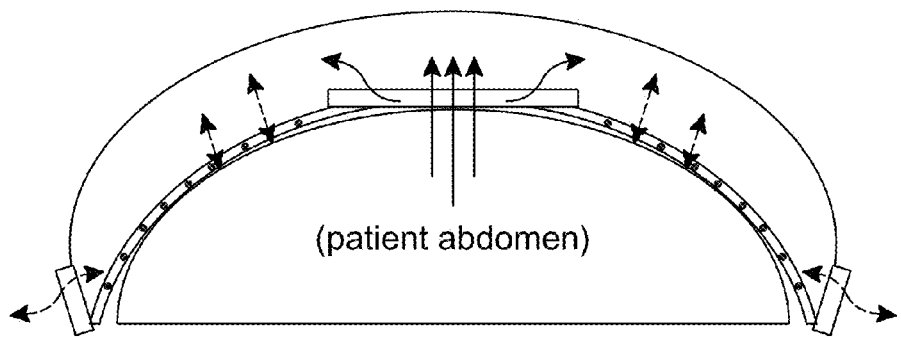
FIG. 10 illustrates the Bernoulli equation, and the moisture diffusion relationship derived from Fick's Law, and a schematic showing device over the patient's abdomen.

FIG. 9 illustrates schematically the positioning of the device transversely across the abdomen, in this case for a caesarean section incision, with straps as part of one embodiment. The straps can be adjustable, and optionally cross in the back, such as a maternity support belt. The straps can be configured such that comfort by the wearer is achieved and the device can be utilized for most if not all of the day. FIG. 10 also illustrates the Bernoulli equation, and the moisture diffusion relationship derived from Fick's Law, and a schematic showing device over the patient's abdomen.

Figure 11:
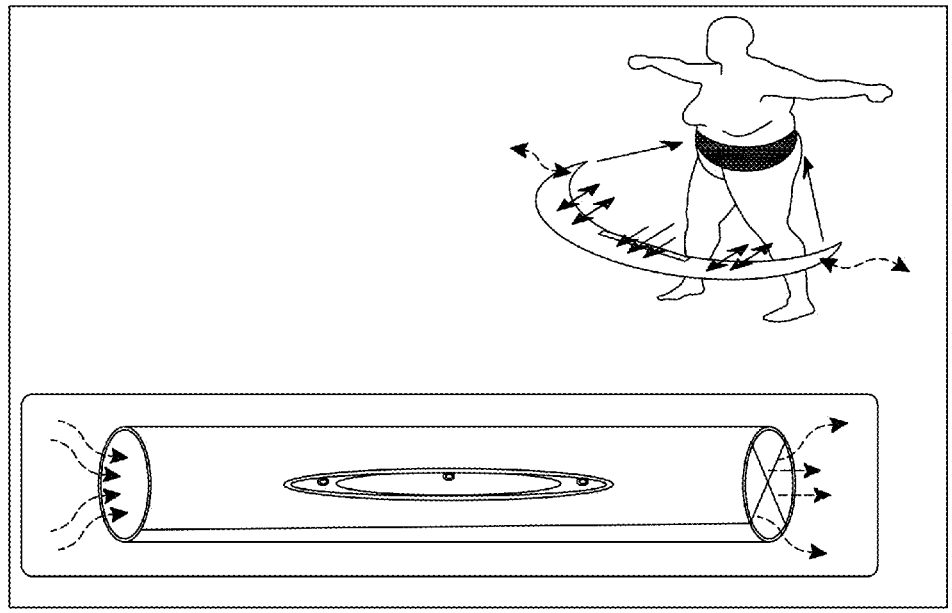
FIG. 11 illustrates a view of device removed from the patient on the top, and a perspective view of an embodiment of the system on the bottom.

FIG. 11 illustrates a view of device removed from the patient on the top, and a perspective view of an embodiment of the system on the bottom.

Figure 12:
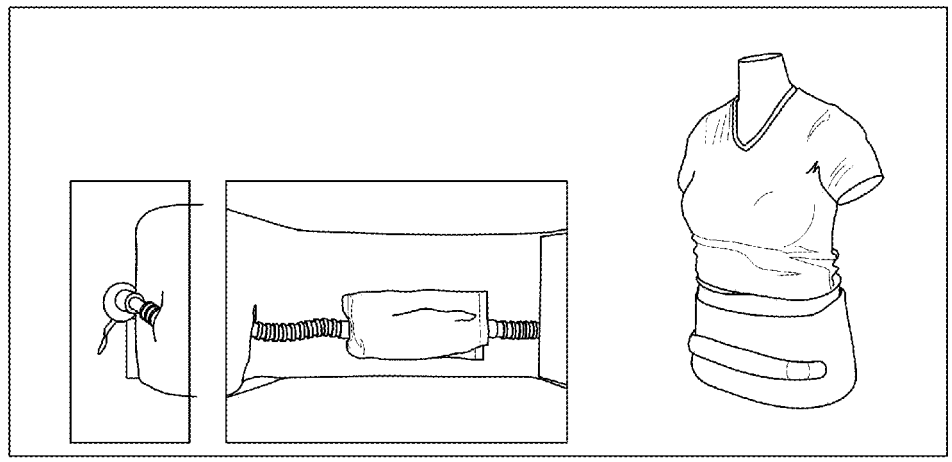
FIG. 12 illustrates from left to right, an embodiment of the system showing the lateral snorkel portion of the conduit, the conduit-wound dressing, and the wrap in position on a model patient.

FIG. 12 illustrates from left to right, an embodiment of the system showing the lateral snorkel portion of the conduit, the conduit-wound dressing, and the wrap in position on a model patient.

Other features of embodiments of wound care systems will now be disclosed. The system can be comprised of multiple surfaces and materials. Medial and lateral to the wound dressing can be surfaces which contact the peri-wound region of the body. This region is susceptible to degradation, breakdown, and maceration resulting from poor microenvironment management. In some embodiments, for patients who would be indicated, these medial/lateral surfaces on the posterior aspect of the device (body contacting) have diffusion properties. These diffusion properties allow for the passage of liquid and gaseous exchange from the intact, but "sweaty" skin. Thus, they can be absorbent, lubricious, and/or breathable. Many materials exist today which have these characteristics. Calcium alginates, saline gauze dressings, standard dry dressings, performance breathable fabrics and multi-laminate fabrics, hydrofibers, hydrocolloids, polyurethanes, celluloses, anti-microbial-enhanced dressings like Medi-Honey or those with silver, are all examples of possible materials which may line and comprise these regions of the device. In some embodiments, the wound dressing or other components can include one or a combination of the following: silk fibers; polyester fibers; nylon fibers; ceramic fibers; polysaccharide fibers including plant fibers such as raw or regenerated (e.g., chemically processed) bamboo, cotton, rayon, linen, ramie, jute, sisal, flax, soybean, corn, hemp, and lyocel; animal fibers such as wool; lactide and/or glycolide polymers; lactide/glycolide copolymers; silicate fibers; polyamide fibers; feldspar fibers; zeolite fibers, zeolite-containing fibers; acetate fibers; plant fibers that have been genetically engineered to express mammalian coagulation proteins or mammalian vasoactive factors. Other fibers that are suitable for use are fibers that have been covalently modified with polymers to promote water absorbancy (e.g., polyvinyl alcohols) and polymers that contain molecular moieties that activate hemostatic systems (e.g., linear or cyclized-arginine-glycine-aspartate moieties such as those found in eptifibatide). In some embodiments, materials can include plant fibers such as raw or regenerated (e.g., chemically processed) bamboo fibers, cotton fibers, and the like, that have high moisture absorbancy and that are capable of activating the intrinsic coagulation cascade.

The anterior surface (away from the body) of the medial and lateral regions of the posterior part (body contacting) of the device also can have unique properties. A combination of microscopic diffusion and macroscopic diffusion comprise these properties. Macroscopically, there may be a pattern or an array of passageways which allow bulk liquid transfer from the body surface to the interior portion of the device and its support matrix. The patterned arrays act as pores or portals for liquid transfer. However, to support moisture transfer in the gaseous state, the composition of this segment of the device may also have microscopic pores, like Gore-Tex or a hydrophilic or hydrophobic synthetic material—which can be foam and amorphous, a complex woven, or a complex non-woven material. The objective of the material selection is to enhance and optimize the gaseous phase moisture transfer and to allow the device to modulate the moisture and humidity of the periwound region. Combined with the moisture and humidity and temperature management provided by the device, skin breakdown is avoided and healing and recovery are supported.

Wounds in some cases require a low to no tension environment to heal. The device, through forces applied to the body, relieves tension across the wound. First, through the combination of straps and adhesive, the device applies compression to the wound and periwound region. Compression directly over the incision via the conduit and the wound dressing allows for a reduction in tension. The fixation of the device in its preferred position allows for a low tension environment across the wound and surrounding region.

In some embodiments, the device can be closed or semi-closed to the ambient environment. In the closed configuration, the ends of the device may be closed or have controlled opening and closure mechanisms. The presence of pumps, fans, and valves can control the ingress and egress of atmospheric air. The valves can be positioned somewhere toward the ends of the device, however, their location can be anywhere that is not interfering with their function. The atmospheric air can be conditioned as it flows inside of the interior channel of the matrix support structure. With the inclusion of thermal heating elements, resistive wires or a Peltier heat exchange unit, which can be positioned circumferentially (resistive wires) longitudinally (resistive wires) or at either end or anywhere along the length of the support matrix (both heat exchanger or resistive elements), the air temperature can be modulated through a simple control loop.

The atmospheric air can optionally be conditioned by passing over a UV LED or similar electrical element which acts to ionize and decontaminate the air. In this fashion, the air which is introduced to the wound and periwound area is devoid of potential microorganisms that can cause infection to the wound.

In some embodiments, the lumen(s) of the conduit, can have a varying geometry to affect the flow velocity and pressure of the atmospheric conditions immediately within the channel. This geometry may allow for nozzles, diffusers, and or parallel channels in which the air flows.

The air is accelerated or decelerated according to the desired local environment prescribed by the physician. In an open or semi-open embodiment, a fan or blower may be positioned internal of the channel. This can turn at a constant rate or a specified on/off interval to modulate the velocity of the air—and correspondingly, the local pressure internal to the channel.

In a more restricted or entirely closed loop, a pump and valve arrangement can more discretely control the velocity and pressure (can be held constant by the position and operation of pumps and valves once a certain pressure is achieved). The pump can be a standard pump that fits within the confines of the channel, or an advanced active-polymer controlled by piezoelectrics. The valve may be similar construction—electroactive, or a more traditional solenoid or one-way check valve.

The humidity can be modulated in part by the absorption and management of the exudate and moisture produced by the body and the wearer, as well as it can be conditioned by a moisture pack internal to the channel of the support structure.

The device support (e.g., conduit 202), which is positioned transverse to the patient, or aligned with the incision in the case of another incision location or orientation, can be flexible in the bending direction. This conformability can be advantageous to provide good contact to the wound and periwound region. The conformability may be achieved by a corrugated type of exterior, but a smooth interior. The smooth interior channel can be advantageous in some cases for reducing head losses with the airflow movement. In some embodiments, instead of corrugation, the conduit can be bendable in a manner that does not kink the channel. The resistance to kinking depends on material selection and the wall thickness. Thus the conduit may comprise a semi-rigid polyurethane, a foam, a non-irritating latex, a polystyrene, a polyvinyl, a polyethylene, an ABS, silicone, or other medical grade semi-rigid material.

The device can be advantageously positioned to sit atop or adjacent to the wound and body surfaces, contacting the external surfaces of the body and the incision. The wound care device can protect against inadvertent puncture, rupture, blunt trauma, sharp trauma, or other harm to the sensitive incision. It can provide compression and binding to the muscle and fascia and skin of the body while allowing for dressing changes and management of the local wound and periwound environment. The support can have a large window area which is covered by the wound dressing and allows for the transfer and exchange of heat, humidity, gaseous, and liquid matter across the wound and incision site. The device can be open and passive in one iteration, which is a lower-cost version, or it can embody enhanced feedback loops and controllers such as pumps, valves, humidifier elements, desiccants, and varying geometry of the internal channel, which together work in concert to actively control and modulate the wound healing environment.

Parameters suitable for certain embodiments of the device will now be described.

Temperature: The temperature at the surface interface of the patient and the conduit lumen can optionally be maintained between 35° C.+/−2° C. The temperature in the conduit lumen can be below body temperature, and as low as 30° C., 25° C., 20° C., or 15° C. in some cases to compensate for body heat production. In some embodiments, components can be selected for the monitoring of the skin surface near or within the wound—for example thermistors and temperature probes, microcontrollers, resistive heating elements or chemical heating (via controlled exothermic reaction) elements, air flow devices such as diaphragm pumps, piezo pumps, turbine fans, non-bladed fans—and which can create a temperature control feedback loop along the length of the conduit lumen.

Force: the conduit can in some embodiments maintain a lumen that does not fully collapse under compression and tension and torsion, imparted by patient's mobility as well as additional mechanical forces imparted by a support component to assist the device's placement and positioning on the body. It may optionally provide levels of compression normal to the plane of the incision. The compression should optionally be adjustable, rendered by increasing or decreasing the circumferential force, for example higher in the first 24 hours of wear and then decreased over time.

One option of controlling the force of the wrap, e.g., the abdominal binder may be via an internal array of guidewires or 'fishing line', where tension is controlled with a dial. The dial, when turned, either takes in line or releases the line, which is stitched into and embedded in the belt. The increase in tension of the embedded lines in turn increases or decreases the overall diameter of the belt, or optionally increases or decreases certain panels of the belt, increasing or decreasing the tension and compression forces imparted by the belt onto the patient wearing the belt.

Humidity: Relative humidity (RH) level in the conduit lumen can optionally range from about 40%+/−5%, 10%, 15%, or 20%, in order to support moisture management at the skin surface.

Moisture: The skin moisture content should optionally be 35%+/−5%, within the temperature range stated above. The minimum (maximum evaporation capability) RH should be able to achieve, in some cases, about 20% at skin content. Moisture can be measured via conductance/impedance, capacitance, infrared, or other technology.

MVTR: The moisture vapor transmission rate, or evacuation of moisture should be optionally able to support a transepidermal water loss (TEWL) rate ranging between 5 $g/m^2/h$ to 50 $g/m^2/h$. This is the range of rates of exudate and skin fluid production between normal, high TEWL, and highly exuding wounds and skin surfaces.

Oxygen Saturation: The oxygen saturation within the conduit lumen can optionally be no less than 8.5 $mol/m^3$ (approximately equal to oxygen content of atmospheric air at 30° C.). Maximum oxygen saturation should not, in some embodiments, exceed 20 $mol/m^3$. However, in some embodiments the systems and methods can be combined with hyperbaric oxygen therapy to achieve a synergistic result.

Velocity of air: the velocity and volume of air movement is a driven value based on the control parameters for moisture and temperature and humidity.

The evaporation channel has exposure to the external environment via one or a multiplicity of portal(s)/hole(s)/vent(s) located optionally at the lateral ends of the channel, or at locations on or along the channel.

The evaporation can be controlled passively through diffusion gradients between the channel and the ambient environment, or optionally, encouraged through a pump or fan mechanism that creates a pressure and velocity differential to flow air through the channel. In some embodiments, the device can incorporate vacuum/a negative pressure system.

Introducing a forced stream or flow of air through the air gap channel increases the evaporation rate as well as delivers additional oxygen to the wound and periwound area.

An oxygen-concentrating membrane and oxygen releasing material may optionally be incorporated into the air channel. The function of this membrane or material is to increase the oxygen concentration at the wound site, thereby encouraging healing.

The conduit to the atmosphere may optionally be a single lumen, or comprised of multiple parallel lumens. However, optionally, the terminus of the lumens may be staggered. The effect of this is that if one end is blocked—due to clothing, patient movement, patient position for example—then air may flow through an unblocked or unrestricted lumen.

In some embodiments, the device components work together as a system to create an air gap/air channel whereby the wound dressing that is against the skin and the surrounding absorbent pads, in conjunction with the compression and fixation wrap or adhesive tabs, combined with the semi-rigid structure of the conduit that creates the air channel, work together to absorb and evaporate wound exudate and periwound moisture away from the body despite the presence of a panniculus. Because the panniculus overlies the device, instead of overlaying and occluding the wound site, the bandage therefore is allowed to function more optimally and the moisture produced by the body from normal or elevated physiologic processes (for example wound healing or sweating) is allowed to be absorbed into an aerated bandage which does not become saturated because of the ingress and egress of air flow through the air channels. In some embodiments, the device can stably move, e.g., retract the panniculus about or at least about 5 mm, 1 cm, 1.5 cm, 2 cm, 2.5 cm, 3 cm, 3.5 cm, 4 cm, 4.5 cm, 5 cm, or more away from the wound bed compared to the location of the panniculus when undisturbed by the device. The device can keep the panniculus in position for at least about 1, 2, 3, 4, 5, 6, 7, 8, 12, 16, 24 hours, or more.

The device may optionally function passively; where the feedback loop is not energized and the evaporation is achieved by the harmonious integration of the device elements of the support, the air gap structure, and the bandage wound dressing.

In some embodiments, the device may function with a feedback loop to measure, control and modulate the parameters of the wound healing. The device may optionally contain communication capabilities with an embedded wireless, e.g., Wi-Fi, Bluetooth, or cellular radio chip to transmit certain values from the control loop and send the signal and information to a central database or an individual care provider, to allow the remote monitoring of the wound healing status for the individual wearing the device.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "positioning a wound healing device on a wound site on a patient's abdomen" includes "instructing the positioning of a wound healing device on a wound site on a patient's abdomen." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system for improving wound healing, comprising:
   a wound dressing having a wound-facing surface and a second surface, the wound-facing surface configured to contact a wound of a patient;
   at least one conduit having an interior lumen, the conduit operably connectable to the second surface of the wound dressing, wherein the conduit comprises a central window configured to allow air flow from the interior lumen of the conduit to the wound-facing surface of the wound dressing; and
   a flexible wrap operably connectable to the conduit.

2. The system of claim 1, wherein the window comprises a zone of porous material within the conduit.

3. The system of claim 1, wherein the window comprises apertures within the conduit.

4. The system of claim 1, wherein the window comprises a cut-out portion of the conduit.

5. The system of claim 1, wherein the conduit is configured to resist collapsing upon itself.

6. The system of claim 1, wherein the conduit comprises interconnected struts and open cells in between the struts.

7. The system of claim 1, wherein the conduit has a generally circular cross-section.

8. The system of claim 1, comprising a plurality of conduits.

9. The system of claim 1, wherein the conduit comprises a corrugated outer surface.

10. The system of claim 1, wherein the conduit comprises removable caps to occlude the lateral ends of the conduit.

11. The system of claim 1, wherein the interior lumen of the conduit comprises a restriction proximate the central window.

12. The system of claim 1, wherein the flexible wrap comprises a binder configured to wrap circumferentially around an abdomen of the patient.

13. The system of claim 1, wherein the flexible wrap comprises vertically-oriented adjustable straps.

14. The system of claim 1, further comprising one or more sensors operably connected to the conduit, the sensors configured to measure one or more of: pH, temperature, humidity, air flow velocity, and pressure.

15. A method for improving wound healing, comprising the steps of:
identifying a patient at risk of wound dehiscence;
positioning a wound care system comprising a wound dressing having a skin contacting surface and a second surface, a conduit having an interior lumen connected to the second surface of the wound dressing, and a flexible wrap operably connected to the conduit proximate a wound of the patient's skin, wherein the wound dressing is positioned substantially co-linearly along a long axis of a wound of the patient's skin,
wherein the conduit comprises a window configured to allow air flow from the interior lumen of the conduit to the wound facing surface of the dressing, and
wherein positioning the wound care system stably repositions overhanging skin or adipose tissue surrounding the wound to a location farther away from the wound; and securing the wrap around a portion of the patient.

16. The method of claim 15, wherein the wound is a surgical wound.

17. The method of claim 16, wherein the surgical wound is an abdominal wound.

18. The method of claim 17, wherein the abdominal wound is a Caesarean section wound.

19. The method of claim 15, wherein the patient has a BMI of greater than about 30.

20. The method of claim 15, wherein the wrap does not occlude the wound after being secured around a portion of the patient.

* * * * *